US009308035B2

(12) United States Patent
Biedermann et al.

(10) Patent No.: US 9,308,035 B2
(45) Date of Patent: Apr. 12, 2016

(54) BONE ANCHORING DEVICE

(75) Inventors: Lutz Biedermann, VS-Villingen (DE);
Wilfried Matthis, Weisweil (DE);
Gerhard Pohl, St. Georgen (DE)

(73) Assignee: Biedermann Technologies GmbH & Co. KG (DE)

( * ) Notice: Subject to any disclaimer, the term of this patent is extended or adjusted under 35 U.S.C. 154(b) by 353 days.

(21) Appl. No.: 13/610,766

(22) Filed: Sep. 11, 2012

(65) Prior Publication Data

US 2013/0123857 A1 May 16, 2013

Related U.S. Application Data

(60) Provisional application No. 61/535,290, filed on Sep. 15, 2011.

(30) Foreign Application Priority Data

Sep. 15, 2011 (EP) .................................. 11 181 525

(51) Int. Cl.
| A61B 17/74 | (2006.01) |
| A61B 17/80 | (2006.01) |
| A61B 17/84 | (2006.01) |
| A61B 17/72 | (2006.01) |
| A61B 17/00 | (2006.01) |

(52) U.S. Cl.
CPC ............. *A61B 17/84* (2013.01); *A61B 17/7258* (2013.01); *A61B 17/744* (2013.01); *A61B 17/80* (2013.01); *A61B 2017/00867* (2013.01)

(58) Field of Classification Search
CPC ............. A61B 17/809; A61B 17/7258; A61B 17/8655; A61B 17/844; A61B 2017/8655
USPC ................ 606/310, 313, 326, 327; 623/17.16
See application file for complete search history.

(56) References Cited

U.S. PATENT DOCUMENTS

| 3,269,251 | A | * | 8/1966 | Bass .............................. 411/21 |
| 4,636,121 | A | * | 1/1987 | Miller ............................ 411/21 |
| 5,578,035 | A | * | 11/1996 | Lin ...................... A61B 17/744 606/65 |
| 5,643,321 | A | | 7/1997 | McDevitt |
| 5,702,391 | A | * | 12/1997 | Lin ........................... 623/17.11 |
| 5,702,481 | A | * | 12/1997 | Lin ............................... 424/423 |
| 5,800,550 | A | * | 9/1998 | Sertich ....................... 623/17.16 |
| 5,976,139 | A | * | 11/1999 | Bramlet ......................... 606/66 |

(Continued)

FOREIGN PATENT DOCUMENTS

| WO | WO 02/34107 A2 | 5/2002 |
| WO | WO 03/032852 A2 | 4/2003 |

(Continued)

*Primary Examiner* — David Bates
(74) *Attorney, Agent, or Firm* — Lewis Roca Rothgerber Christie LLP (57) ABSTRACT

A bone anchoring device for anchoring in a bone comprises a hollow shaft having an outer surface including a first portion and a threadless second portion, the second portion having a larger outer diameter and a shorter axial length than the first portion; and a barb carrier having at least two barb elements. The shaft and the barb carrier can be moved relative to each other in such a manner that in a first configuration the barb elements of the barb carrier project beyond an outer surface of the shaft by a distance $d_1$, and in such a manner that in a second configuration the barb elements of the barb carrier project beyond the outer surface of the shaft along the second portion of the shaft by a distance of $d_2$, wherein $d_2 > d_1$.

21 Claims, 11 Drawing Sheets

(56) References Cited

U.S. PATENT DOCUMENTS

| | | | |
|---|---|---|---|
| 6,443,395 B1 | 9/2002 | Porte et al. | |
| 6,488,684 B2 * | 12/2002 | Sterghos | A61B 17/7266 606/62 |
| 6,527,803 B1 * | 3/2003 | Crozet et al. | 623/17.11 |
| 6,554,833 B2 * | 4/2003 | Levy | A61B 17/7258 606/62 |
| 6,575,973 B1 * | 6/2003 | Shekalim | A61B 17/7266 606/62 |
| 6,648,889 B2 * | 11/2003 | Bramlet | A61B 17/744 606/310 |
| 7,879,036 B2 * | 2/2011 | Biedermann et al. | 606/62 |
| 8,292,932 B2 * | 10/2012 | Matthis et al. | 606/300 |
| 8,486,120 B2 * | 7/2013 | Shimko | 606/303 |
| 8,876,822 B2 * | 11/2014 | Fagan | A61B 17/7266 606/64 |
| 2001/0000186 A1 | 4/2001 | Bramlet et al. | |
| 2005/0049590 A1 * | 3/2005 | Alleyne et al. | 606/61 |
| 2005/0159749 A1 * | 7/2005 | Levy et al. | 606/72 |
| 2006/0145396 A1 | 7/2006 | Okada et al. | |
| 2006/0155281 A1 | 7/2006 | Kaup et al. | |
| 2006/0229617 A1 * | 10/2006 | Meller | A61B 17/746 606/62 |
| 2006/0264952 A1 * | 11/2006 | Nelson et al. | 606/72 |

FOREIGN PATENT DOCUMENTS

| | | |
|---|---|---|
| WO | WO 2004/026158 A1 | 4/2004 |
| WO | WO 2004/030549 A1 | 4/2004 |
| WO | WO 2009/106951 A1 | 9/2009 |

* cited by examiner

BONE ANCHORING DEVICE

CROSS-REFERENCE TO RELATED APPLICATION(S)

The present application claims the benefit of U.S. Provisional Patent Application Ser. No. 61/535,290, filed Sep. 15, 2011, the contents of which are hereby incorporated by reference in their entirety, and claims priority to European Patent Application EP 11 181 525.4, filed Sep. 15, 2011, the contents of which are hereby incorporated by reference in their entirety.

BACKGROUND

The invention relates to a bone anchoring device, in particular for application to the femur for anchoring in a bone. The bone anchoring device includes a hollow shaft having an outer surface and a barb carrier having a plurality of barb elements. The shaft and the barb carrier can be moved relative to each other in such a manner that in a first configuration the barb elements of the barb carrier do not project beyond an outer surface of the shaft and in such a manner that in a second configuration the barb elements of the barb carrier project beyond the outer surface of the shaft. The moving direction of the barb carrier from the first to the second configuration is against the insertion direction of the bone anchoring device, wherein the bone anchoring device is threadless. The bone anchoring device may be applied, for example, to an osteoporotic femur.

A known form of a bone anchoring device is a bone screw comprising a shaft with a thread for screwing a screw into a bone. The bone screw is manually inserted into the bone by means of a screw driver, which is a time-consuming and force-requiring process. Moreover, during the process in which the screw is inserted into the bone, high pressure forces may be acting on the bone itself, which is undesirable in certain clinical applications such as in neurosurgery, spinal surgery, pediatric surgery or trauma surgery. In particular, referring to osteoporosis, such high pressure forces acting on the surrounding bone structure are highly problematic.

DESCRIPTION OF RELATED ART

US 2001/0000186 A1 discloses a surgical fastener assembly for coupling first and second bone portions across a fracture therebetween having a thread and a hollow portion with four openings for guiding four elongated pins held by an insert which is movable within the hollow portion. These pins engage with the bone structure when the insert is axially pulled back by means of a tool.

SUMMARY

It is an object of the invention to provide a bone anchoring device, which can be inserted into the bone more rapidly, more easily and with less force than conventional bone screws and nails and can also be removed easily from the bone.

The bone anchoring device according to an embodiment of the invention facilitates rapid and secure anchoring in the bone by pressing the bone anchoring device into a prepared bore hole in the bone. During the insertion of the bone anchoring device, barb elements of an insert, which forms a barb carrier, extend into the openings of a hollow shaft of the bone anchoring device not farther than an outer surface of the shaft. After insertion of the bone anchoring device, the barb carrier and the shaft are moved relative to each other in such a manner that the barb elements of the barb carrier are spread and project through the openings of the hollow shaft beyond the outer surface of the shaft. Therefore, the barb elements prevent the bone anchoring device from being pulled out or coming loose. The bone anchoring device of the present invention can be easily removed, if required, by just moving again the hollow shaft and the barb carrier relative to each other in such a manner that the barb elements of the insert only extend into the openings maximally as far as the outer surface of the shaft, i.e. in this configuration the barb elements do not project beyond the outer surface of the shaft. In this configuration there is no barb effect, because the barb elements do not engage with the surrounding bone structure.

The barb elements may be flexible and are made of any flexible material, for example of Nitinol. It is one advantage of Nitinol that a deformation of the barb elements made of this material is completely reversible.

By this reversible barb connection, the threadless bone anchoring device does not exert damaging forces on the bone during insertion and provides for secure attachment. Therefore, the present invention is especially suitable for osteoporosis patients, because there is no damaging by a thread or a screw which directly acts on the surrounding bone structure. The barb elements penetrate the bone structure wherein this penetration is more gentle as for example an expanding or swinging-out of the barb elements which would destroy more surrounding bone structure. Furthermore, the implanting process of the bone anchoring device according to the present invention is very fast, since it is not necessary to screw it in but only to insert it. The bone anchoring device according to the invention is also easily to manufacture.

BRIEF DESCRIPTION OF THE DRAWINGS

Further features and advantages of the invention will become apparent and will be best understood by reference to the following detailed description taken in conjunction with the accompanying drawings.

FIG. 2 shows a perspective view of the bone anchoring device in the first configuration according to the embodiment shown in FIG. 1a.

FIG. 5a shows a perspective view of an enlarged portion of the bone anchoring device shown in FIG. 1a.

FIG. 6a shows a side view of the bone anchoring device in the first configuration according to the embodiment shown in FIG. 1a.

FIG. 6b shows a cross-sectional view of the bone anchoring device in the first configuration according to the embodiment shown in FIG. 1a.

FIG. 8b shows a perspective view of the barb carrier in a first configuration according to the embodiment shown in FIG. 8a.

FIG. 8c shows a perspective view of the barb carrier in a second configuration according to the embodiment shown in FIG. 8a.

DETAILED DESCRIPTION

A bone anchoring device 1 according to a first embodiment of the invention is described with reference to FIGS. 1 to 7b. As can be seen from FIGS. 1a and 1b, the threadless bone anchoring device 1, in particular a femur anchor 1, can be connected to a bone plate 100 which comprises a plate-like body which is fixed to a bone by screws for example and a tube-like body which can accommodate a portion of the bone anchoring device 1, wherein the plate-like body and the tube-like body may be connected integrally to each other in an angled manner as can be seen from FIGS. 1a and 1b.

Figure 2:
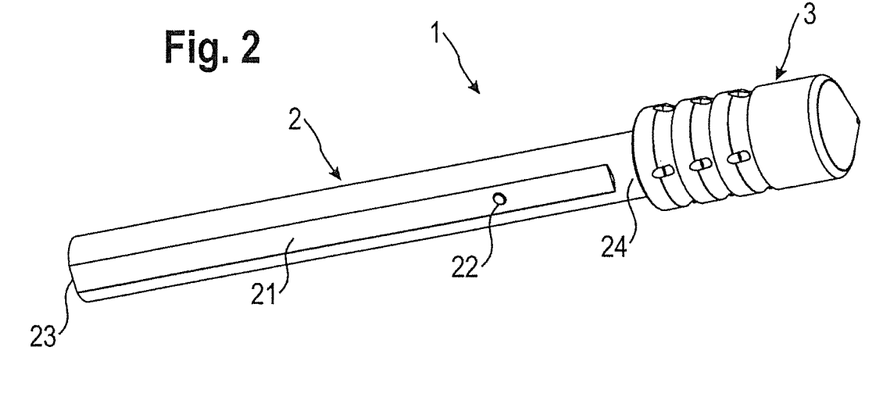

FIG. 2 shows the bone anchoring device 1 having a shaft which comprises a substantially cylindrical hollow shaft portion 2 and a substantially cylindrical hollow head portion 3. The shaft portion 2 has a first end 23, a second end 24 and at least one coaxial groove 21, wherein the groove 21 extends from the first end 23 to a predetermined distance from the second end 24. The groove 21 comprises a hole 22 at a distance to the second end 24 of the shaft 2 portion. The shaft portion 2 and the head portion 3 are formed integrally and the outer diameter of the head portion 3 is larger than the outer diameter of the shaft portion 2. It is also possible to provide the shaft portion 2 and the head portion 3 as separate parts and/or to provide them with the same diameter.

Figure 3:
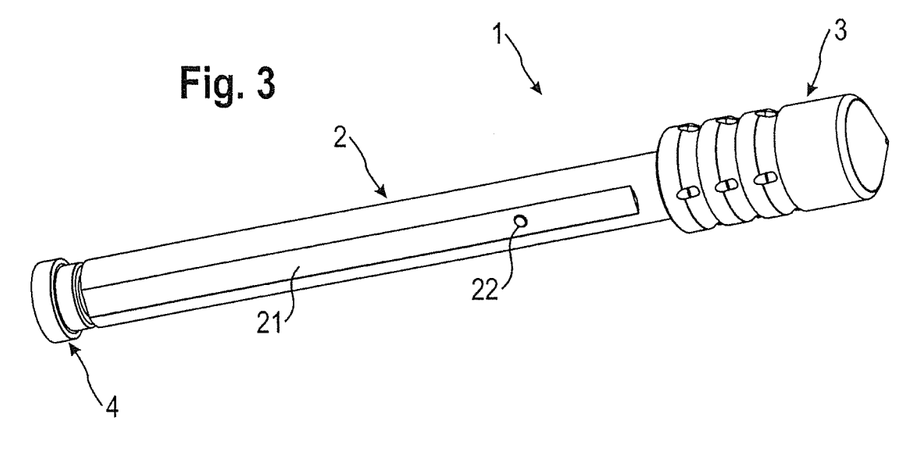
FIG. 3 shows a perspective view of the bone anchoring device in the first configuration according to the embodiment shown in FIG. 1a together with a connection screw.
Figure 4:
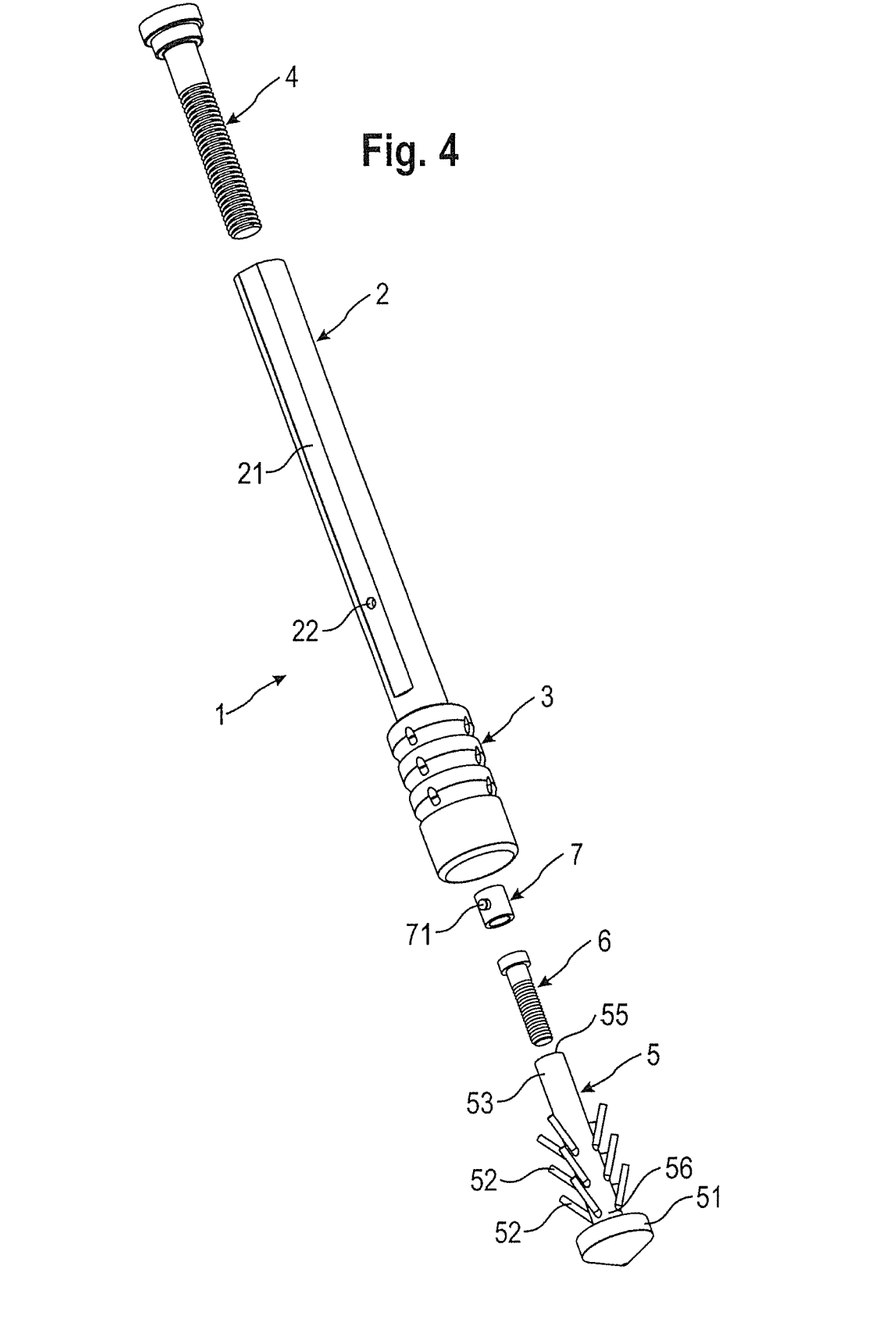
FIG. 4 shows a perspective exploded view of the bone anchoring device shown in FIG. 3.
Figure 6A:
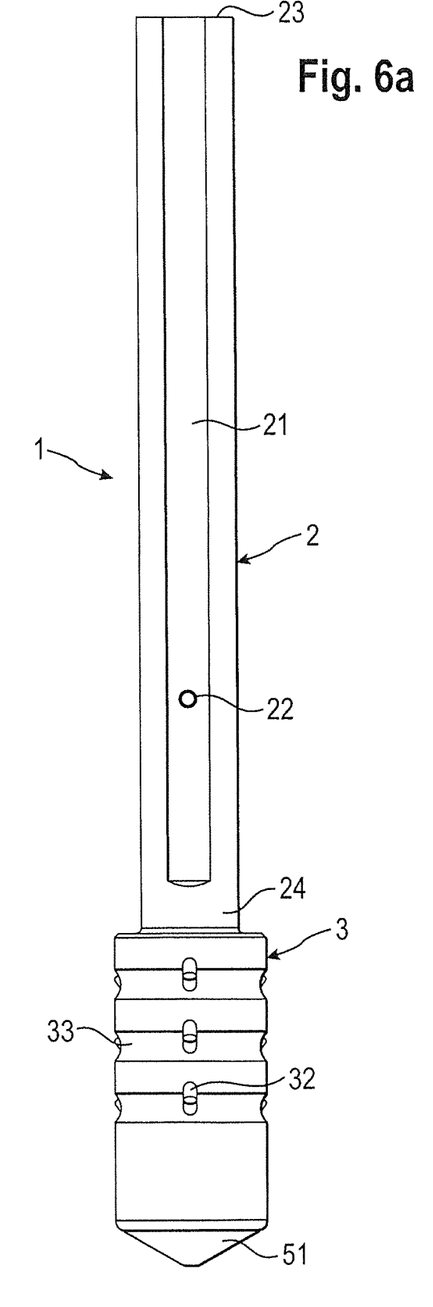
Figure 6B:
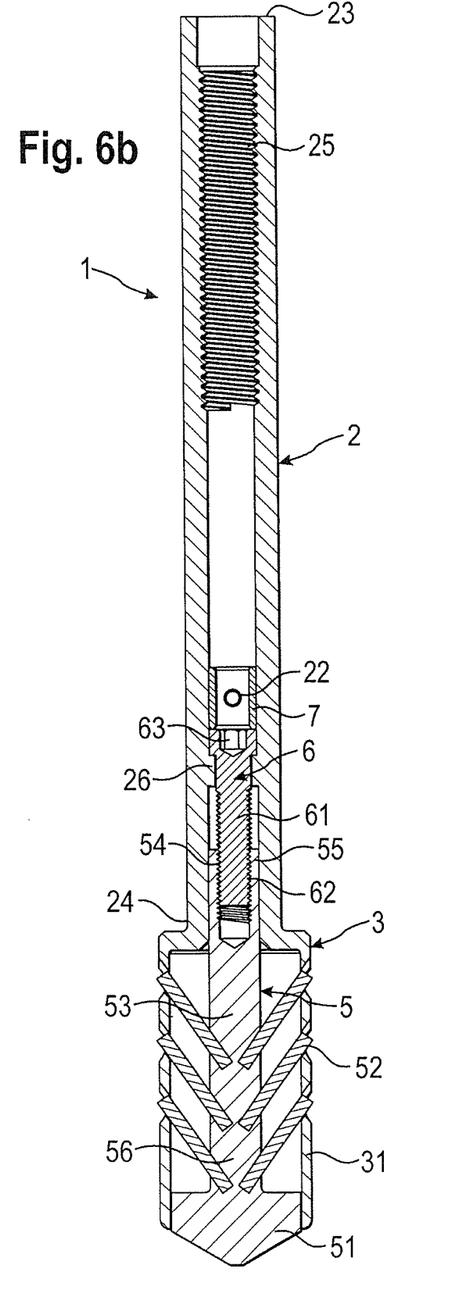
Figure 6C:
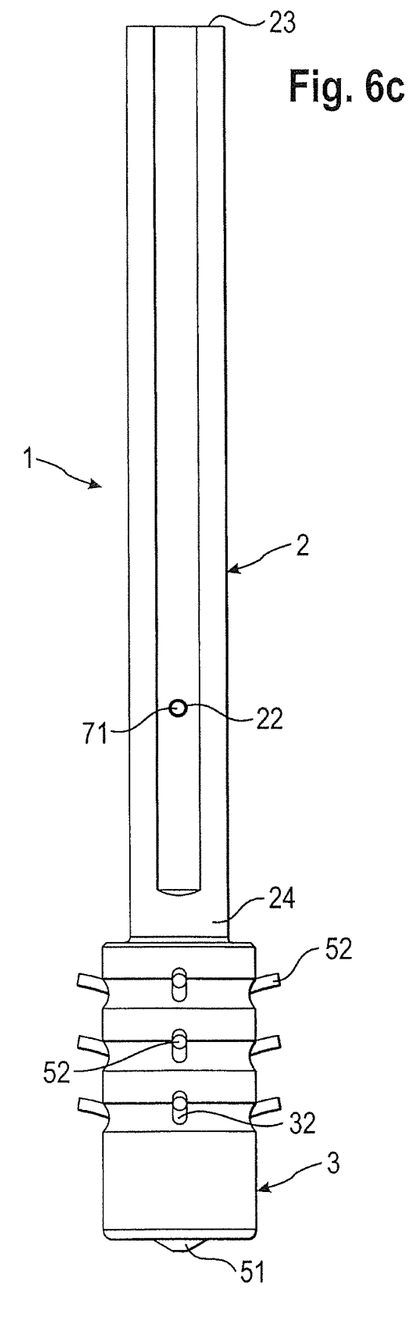
FIG. 6c shows a side view of the bone anchoring device in the second configuration according to the embodiment shown in FIG. 1b.
Figure 6D:
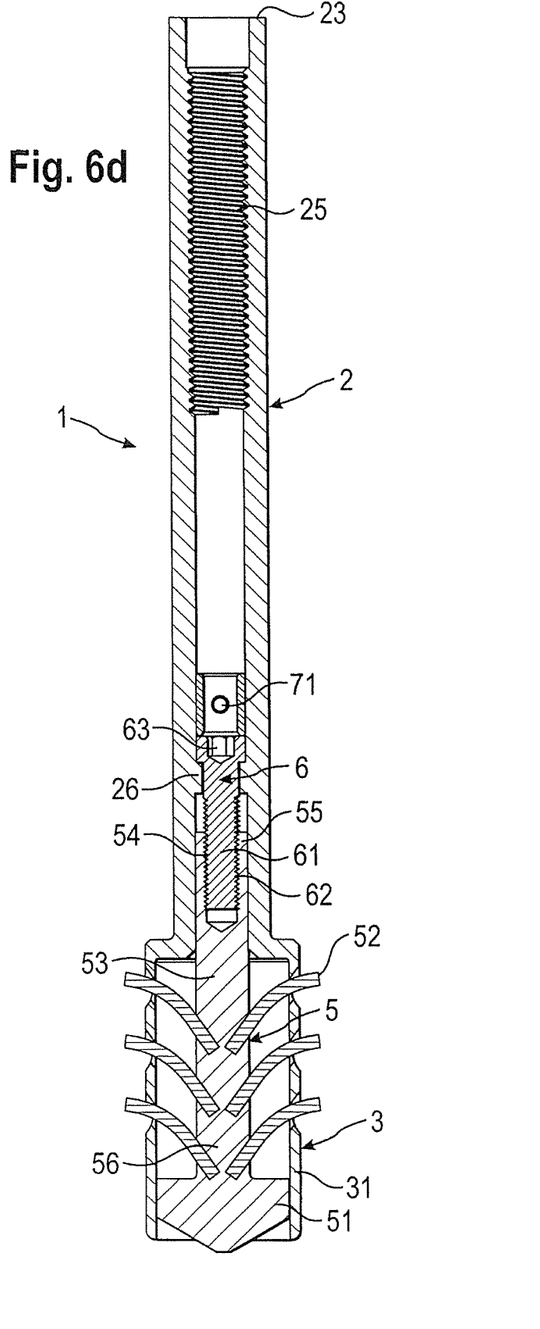
FIG. 6d shows a cross-sectional view of the bone anchoring device in the second configuration according to the embodiment shown in FIG. 1b.
Figure 7A:
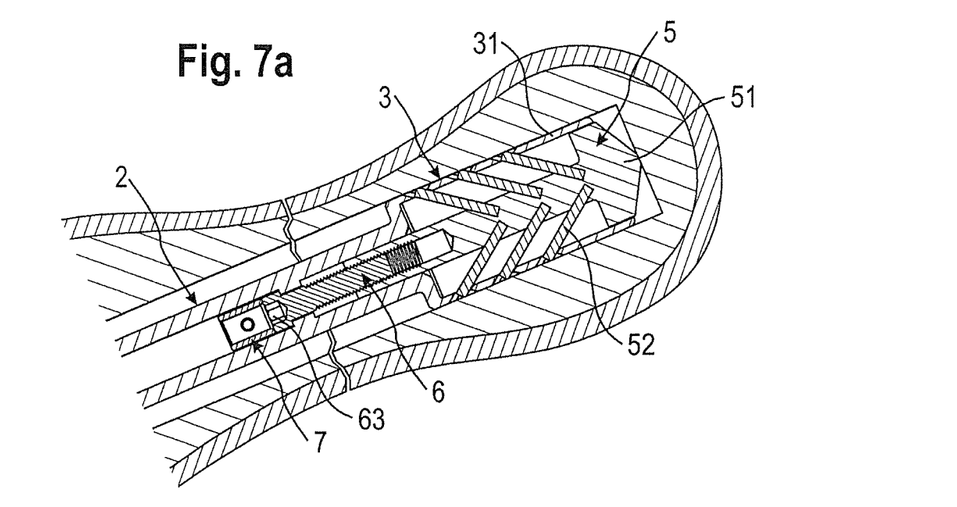
FIG. 7a shows a cross-sectional view of a front portion of the bone anchoring device in the first configuration according to the embodiment shown in FIG. 1a inserted into a bone.
Figure 7B:
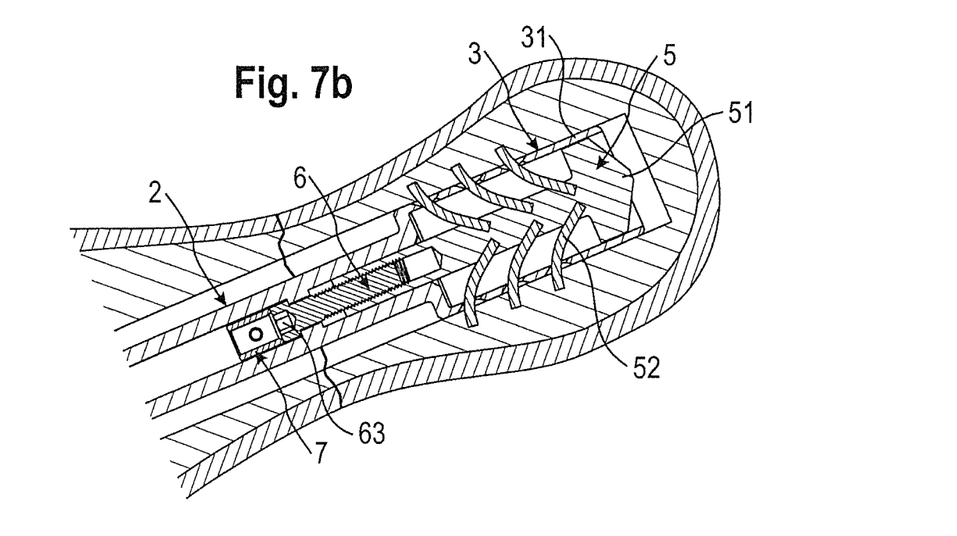
FIG. 7b shows a cross-sectional view of a front portion of the bone anchoring device in the second configuration according to the embodiment shown in FIG. 1b inserted into the bone.

In FIGS. 3 and 4 a locking screw 4 is shown by which the bone anchoring device 1 can be fixed to the bone plate 100 via an inner thread 25, shown in FIGS. 6b, 6d. As can be seen in FIG. 4, the bone anchoring device 1 further comprises a sleeve 7 having a pin 71 which is configured to cooperate with the hole 22 of the groove 21 of the shaft 2 portion. The pin 71 can be a snap fastener, for example, which can be pushed inside the sleeve 7 against a spring force, for example (not shown). The sleeve 7 fits into the hollow shaft 2 portion, i.e. the outer diameter of the sleeve 7 is the same or slightly smaller than the inner diameter of the hollow shaft portion 2, which can be seen, for example, in FIGS. 6b and 6d. The pin 71 fits into the hole 22 of the groove 21 of the shaft portion 2 and can snap into or engage with the hole 22 from the inside of the shaft portion 2. By this, the sleeve 7 works as a stop for a head of a screw 6 which is also insertable into the hollow shaft portion 2. By the sleeve 7, the screw 6 is prevented from moving towards the first end 23 of the shaft portion 2. For preventing the screw 6 from moving in the direction of the second end 24, an abutment portion 26, shown in FIGS. 6b, 6d, is provided integrally with the shaft portion 2 which forms an abutment for the head of the screw 6. Because of this abutment, the screw 6 can only be inserted into the shaft portion 2 from the first end 23.

Furthermore, a barb carrier 5 in the form of an insert is provided having a first end 55, a second end 56, a shaft member 53, a head member 51 and a plurality of barb elements 52 which are connected to the shaft member 53. The head member 51 of the barb carrier 5 comprises a cylindrical portion and a cone-shaped portion which forms a tip.

Figure 5A:
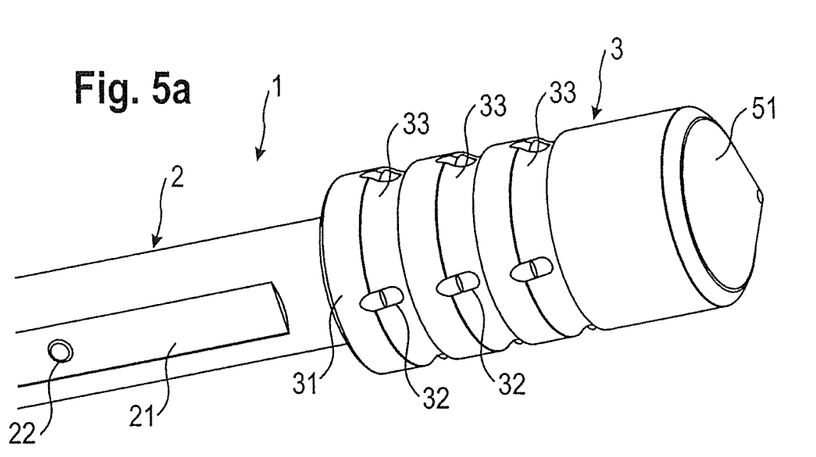

As can be seen from FIG. 5a, the head portion 3 comprises an outer surface 31 that has a plurality of circumferential grooves 33. In FIG. 5a three grooves 33 are shown. The grooves 33 have a circle-segment-shaped cross-section. On the ground of each groove 33 openings 32 are provided which are circumferentially distributed with the same distance to one another and extend through the wall of the hollow head portion 3 for guiding the barb elements 52 in operation. In. FIG. 5a, four openings 32 are shown in each groove 33. That means that the openings 32 are positioned in a 90° angular orientation to each other. It is also possible to provide more or fewer grooves 33, more or fewer openings 32 or to arrange the openings 32 in different ways referring to their angular orientation. As can be seen from FIGS. 5a, 5b the head 51 of the barb carrier 5 forms a tip of the bone anchoring device 1.

As can be seen from FIGS. 6a and 6b, the bone anchoring device 1 in a first configuration is shown. The bone anchoring device 1 comprises an inner thread 25 on its first end 23 which can cooperate with the locking screw 4 shown in FIG. 4 to fix the bone anchoring device 1, for example to the bone plate 100. The sleeve 7 is provided within the hollow shaft portion 2 and forms a stop for the screw 6 having an engagement structure 63 for engaging with a tool (not shown) for rotating the screw 6. The barb carrier 5 is provided partly within the head portion 3 and partly within the shaft portion 2. Adjacent to the first end 55 of the barb carrier 5, the shaft member 53 has a threaded hole with an inner thread 54 for engaging an outer thread of the screw 6.

In the first configuration the cone-shaped portion of the head 51 of the barb carrier 5 is flush with the outer circular edge of the head portion 3. By this, the cone-shaped portion of the head 51 forms the tip for the bone anchoring device 1 in this first configuration. Referring to the relative position of the shaft portion 2 and the barb carrier 5, there is a first distance between the abutment portion 26 and the first end 55 of the barb carrier 5. Furthermore, the barb elements 52 which are connected to the shaft element 53 of the barb carrier 5 extend into the openings 32 of the head portion 3 not farther than an outer surface 31 of the head portion 3. In this first configuration the barb elements 52 do not project over the outer surface 31 of the head portion 3. Therefore, in the first configuration the bone anchoring device 1 can be easily introduced into a hole which was drilled into a bone, which can be seen from FIG. 7a.

In a second configuration shown in FIGS. 6c and 6d the barb carrier 5 is positioned closer to the screw 6 and the sleeve 7 as compared to the first configuration shown in FIGS. 6a and 6b. Further referring to the relative position of the shaft portion 2 and the barb carrier 5, there is a second distance between the abutment portion 26 and the first end 55 of the barb carrier 5, wherein the first distance in the first configuration is larger than the second distance in the second configuration. It is possible that the second distance is nearly zero. In this configuration the barb elements 52 of the insert 5 are bent and project through the openings 32 beyond the outer surface 31 of the head portion 3. In this configuration, the bone anchoring device 1 is fixed in the bone, as can be seen from FIG. 7b. This fixing is reversible. For preventing the barb elements 52 from overloading or shearing, the relative position of the shaft portion 2 and the barb carrier 5 may be set to one another. The movement and therefore the deformation of the barb elements 52 is limited by dimensioning the drilling depth of the inner thread 54 of the barb carrier 5 such that the screw 6 in the second configuration is completely screwed. Between the first and the second configuration, many intermediate configurations exist because of the stepless movement of the barb carrier 5 relative to the shaft 2.

As can be seen in particular from FIGS. 6b and 6d, the barb elements 52 project from the surface of the shaft member 53 of the barb carrier 5 by an angle which is selected during the manufacturing process based upon the material used and the actual dimensions of the barb elements 52 so that a desired stiffness of the barb elements 52 is obtained. The barb elements 52 are attached to the shaft member 53 of the barb carrier 5 by drilling in bore holes into which the barb elements, which can be designed as short pins having a substantially circular cross-section, be inserted by means of a press fit connection. It is also possible to attach the barb elements 52 in different ways to the barb carrier 5, for example by adhesive bonding. Due to their configuration and attachment, the barb elements 52 are elastically deformable relative to the barb carrier 5 and also relative to the openings 32 of the head portion 3 by which they are guided. The barb elements 52 are arranged in an arrow-like, pinfeather-like or fir tree-like configuration, wherein the "arrows" are directed towards the tip 51.

The bone anchoring device 1 can be made of any body-compatible material. Preferably, a body-compatible metal, such as titanium, stainless steel and their alloys, or a body-compatible plastic material can be used. The shaft portion 2 and the head portion 3 can be made of the same material as the barb carrier 5 or of a different material, if a different material is desired to ensure that the barb elements 52 have the necessary elastic properties. Preferably, however, the barb carrier 5 and/or the barb elements 52 are made of a shape-memory alloy having shape-memory and/or super elastic characteristics or are made of a material having spring-like characteristics like stainless steel or titanium alloys. For example, nickel-titanium alloys such as Nitinol are suitable for use for the barb elements 52.

The bone anchoring device is assembled as follows. First, the screw 6 is inserted into the shaft portion 2 from the first end 23 (in FIGS. 6a-d from above). The abutment portion 26 holds the screw 6 in its position. After that the sleeve 7 is inserted into the shaft portion 2 from the first end 23 and the pin 71 snaps into or engages with the hole 22. By this the screw head is now axially fixed between the sleeve 7 and the abutment portion 26 and can only rotate by this guiding structure. Then, the barb carrier 5 is inserted into the head portion 3 from the head portion 3 (in FIG. 6a-d from the bottom) in such a manner that the barb elements 52 extend into the openings 32, but do not project beyond the outer surface 31. The screw 6 is screwed into the inner thread 54 of the barb carrier 5 by means of a tool (not shown) which is inserted from the first end 23 of the shaft portion 2 through the sleeve 7 into the engagement structure 63 of the screw 6.

In use, the bone anchoring device 1 is inserted into a drilled bore hole provided in a bone. Then the screw 6 is rotated by means of the tool (not shown) which moves the barb carrier 5 in the direction of the first end 23 of the shaft portion 2 by the screw and nut connection. By this the barb elements 52 start to move further through the openings 32 of the head 3 and project beyond the surface 31 of the head portion 3. By this, the bone anchoring device 1 is fixed in the bone. Because of their flexibility and because of the shape of the openings 32, the barb elements 52 bend in a direction perpendicular to the longitudinal axis of the bone anchoring device. By this bending the barb elements 52 penetrate the surrounding bone structure. The barb elements 52 expand in the created channel which results in a minimal damaging of the surrounding bone structure. It is possible to provide barb elements 52 with sharpened tips.

In FIGS. 8a to 10d a second embodiment of the bone anchoring device is shown. The function of the system and the device as such is the same as described under the first embodiment of the invention; only the construction of the barb carrier is different.

Figure 8A:
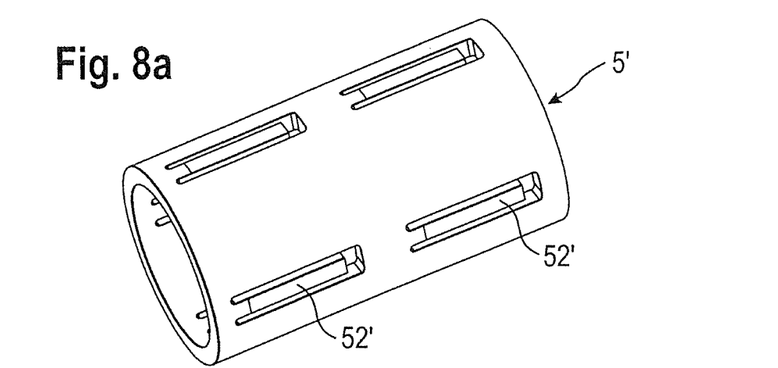
FIG. 8a shows a perspective view of a barb carrier in a manufacturing configuration according to a second embodiment.
Figure 8B:
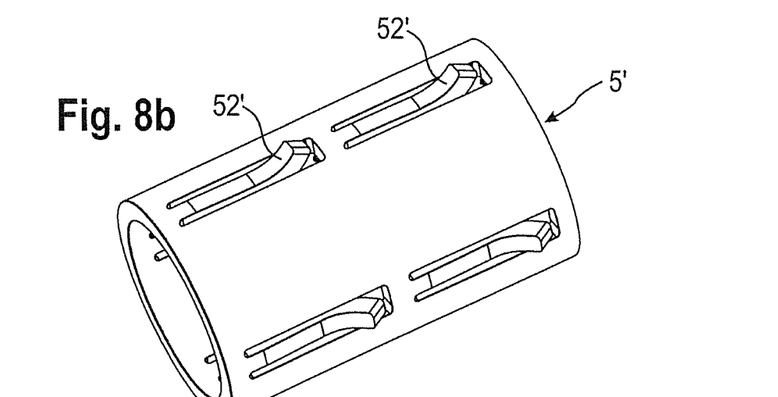
Figure 8C:
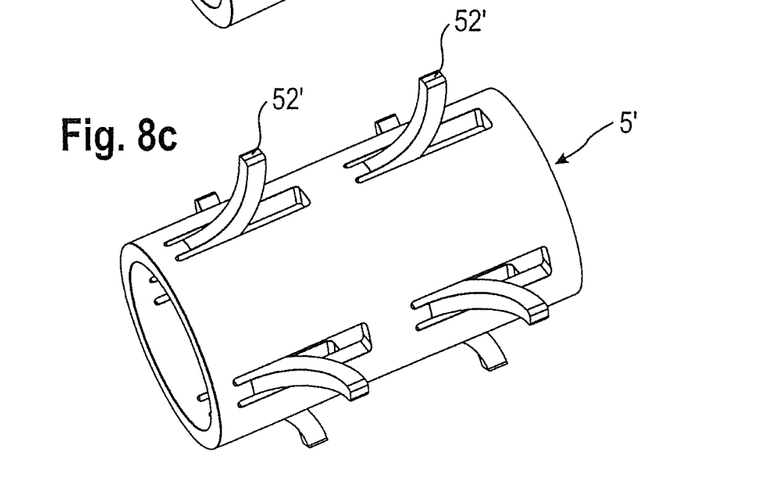

In FIGS. 8a to 8c a barb carrier 5' according to the second embodiment is shown comprising a substantially cylindrical hollow sleeve-like main body having barb elements 52'. The barb elements 52' having a substantially rectangular cross-section are cut out of the wall of the cylindrical body, for example by laser cutting. Preferably, the barb carrier 5' is made of a shape memory material, for example of Nitinol. In FIG. 8a the barb carrier 5' is shown in its manufacturing configuration where the barb elements 52' are not spread but are flush with the rest of the surface of the cylindrical body of the barb carrier 5'. In FIG. 8b the barb carrier 5' is shown in a first configuration where the barb elements 52' are spread partly. In FIG. 8c the barb carrier 5' is shown in its second configuration where the barb elements 52' are spread completely.

Figure 5B:
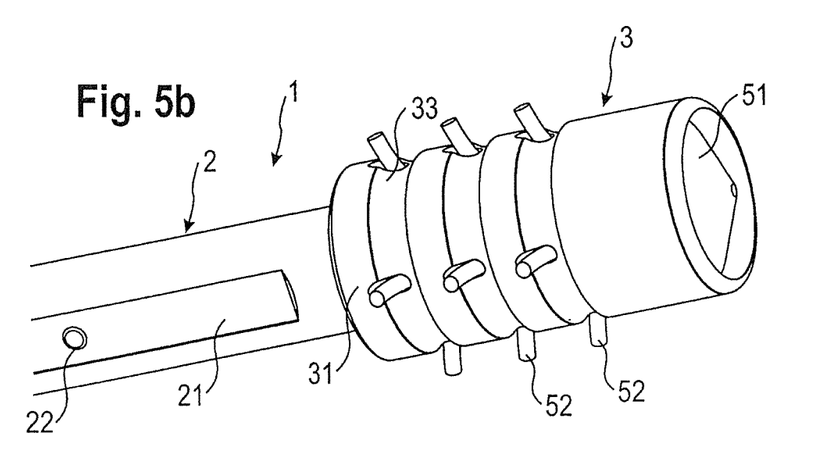
FIG. 5b shows a perspective view of an enlarged portion of the bone anchoring device shown in FIG. 1b.
Figure 9A:
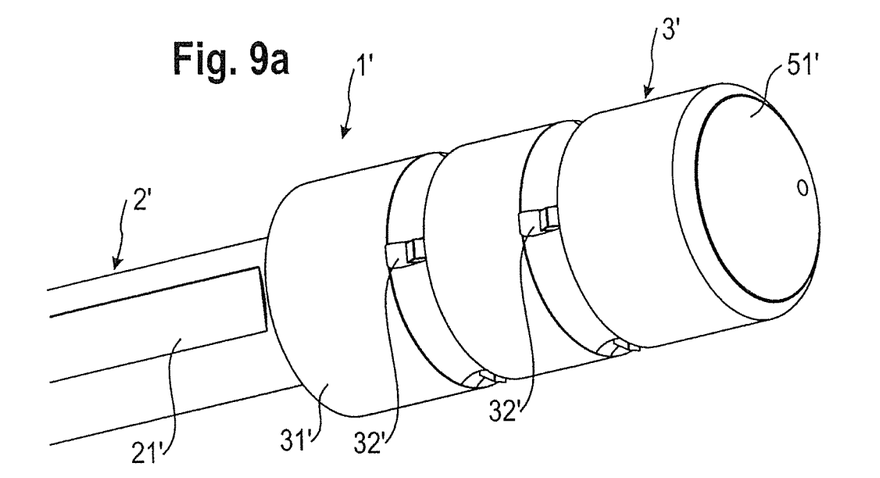
FIG. 9a shows a perspective view of an enlarged portion of a bone anchoring device in the first configuration according to the embodiment shown in FIG. 8b.
Figure 9B:
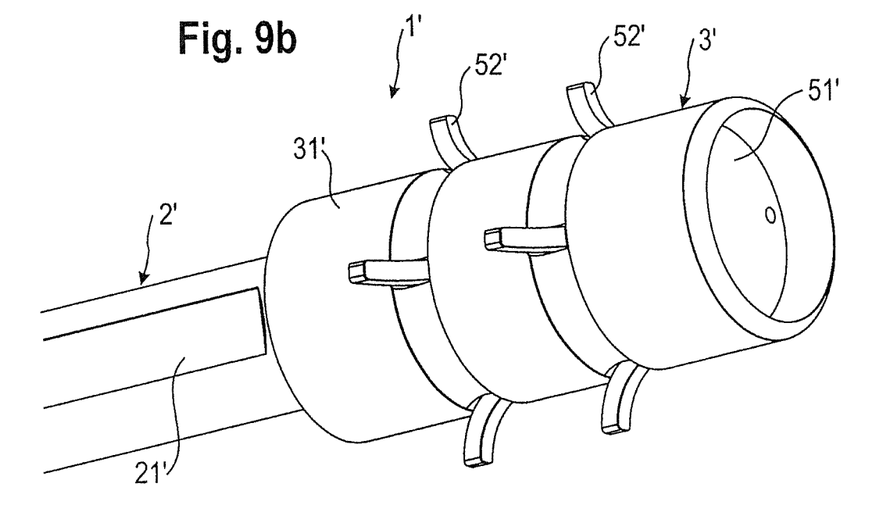
FIG. 9b shows a perspective view of an enlarged portion of the bone anchoring device according to the second embodiment in the configuration shown in FIG. 8c.

FIGS. 9a and 9b correspond to FIGS. 5a and 5b showing the bone anchoring device 1' comprising a shaft portion 2' having a groove 21' and a head portion 3' having a plurality of grooves 32' and an outer surface 31' and a tip 51'.

Figure 10A:
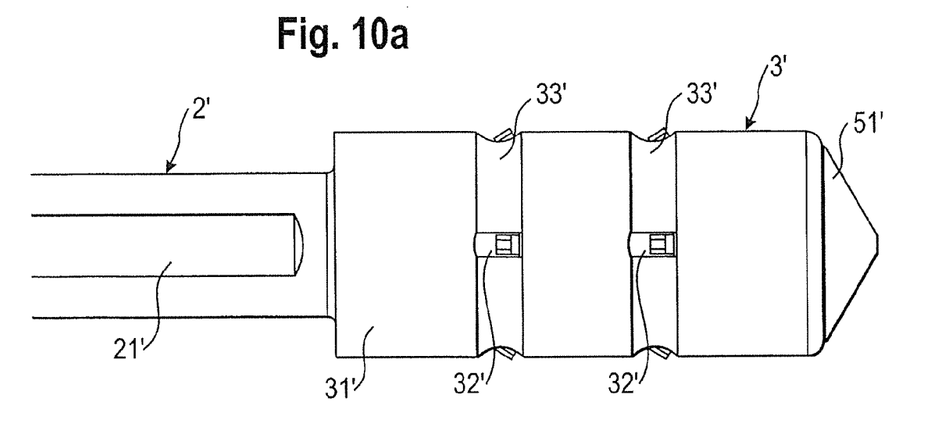
FIG. 10a shows a side view of the bone anchoring device in the first configuration according to the embodiment shown in FIG. 8b.
Figure 10B:
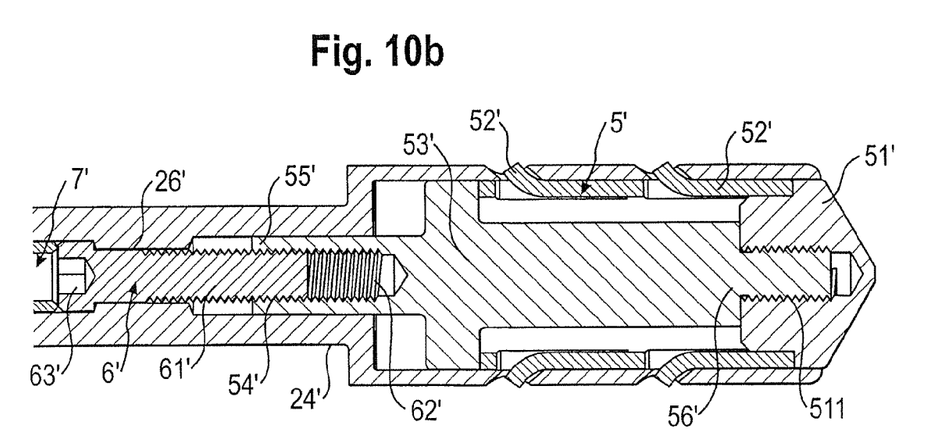
FIG. 10b shows a cross-sectional view of the bone anchoring device in the first configuration according to the embodiment shown in FIG. 8b.

As can be seen from FIGS. 10a and 10b the barb carrier 5' is clamped between the tip 51' and a shaft member 53' having a first end 55' and a second end 56'. The tip 51' comprises an inner thread 511 and the second end 56' of the shaft member 53' forms an outer thread, which is configured to engage the inner thread 511 of the tip 51' to clamp the barb carrier 5'. The wall of the barb carrier 5' is supported by a circumferential portion of the shaft member 53' and a circumferential portion of the tip 51', wherein the outer diameters of the supporting circumferential surfaces and the outer diameter of the barb carrier 5' are substantially the same such as the whole construction is insertable into the head portion 3' of the bone anchoring element 1'.

The movement of the shaft portion 2' and the head portion 3' relative to the barb carrier 5' takes place as in the first embodiment. The shaft member 53' comprises an inner thread 54' on its first end 55' which cooperates with a screw 6'. The screw 6' is fixed between an abutment portion 26' and a sleeve 7' and can only perform a rotational movement for moving the barb carrier 5' relative to the shaft portion 2' and the head portion 3' as in the first embodiment.

Figure 10C:
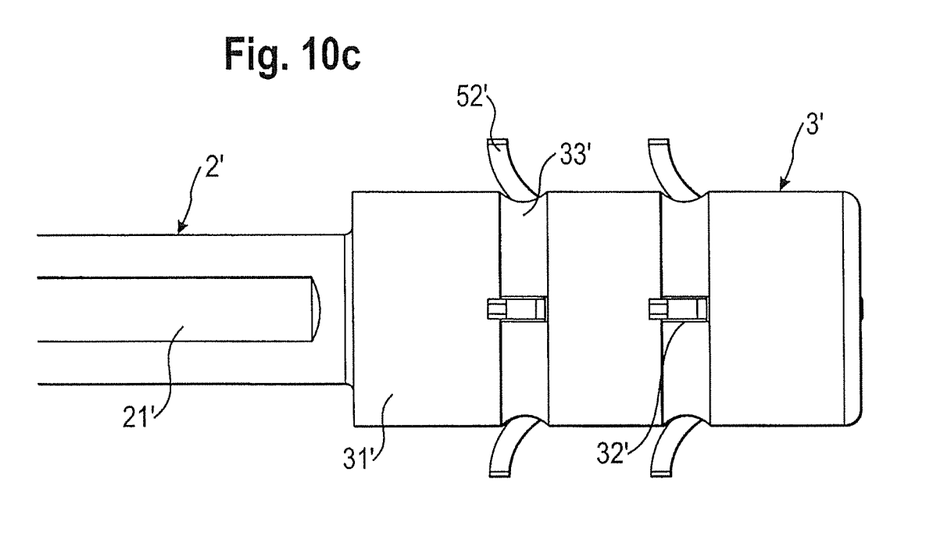
FIG. 10c shows a side view of the bone anchoring device in the second configuration according to the embodiment shown in FIG. 8c.
Figure 10D:
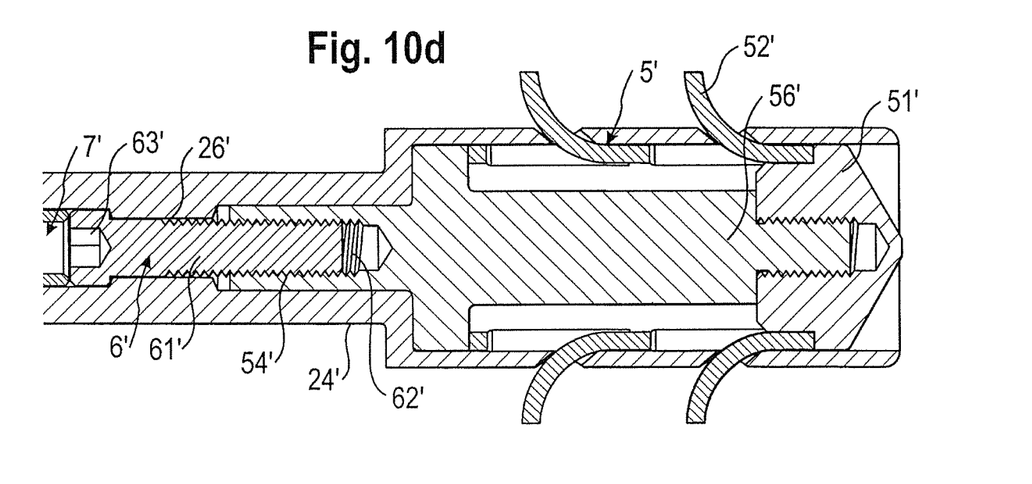
FIG. 10d shows a cross-sectional view of the bone anchoring device in the second configuration according to the embodiment shown in FIG. 8c.

FIGS. 10a and 10b show the bone anchoring device 1' in the first configuration which is the same as the first configuration described referring to the first embodiment and FIGS. 10c and 10d show the bone anchoring device 1' in the second configuration which is the same as the second configuration described referring to the first embodiment.

Figure 1A:
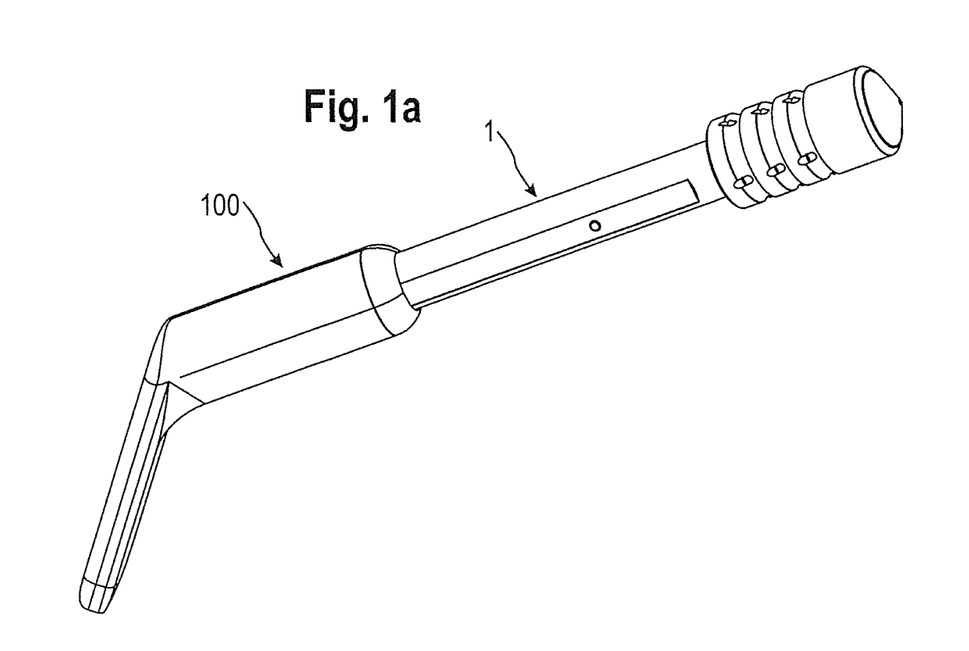
FIG. 1a shows a perspective view of a bone anchoring device in a first configuration according to a first embodiment which is attached to a bone plate.
Figure 1B:
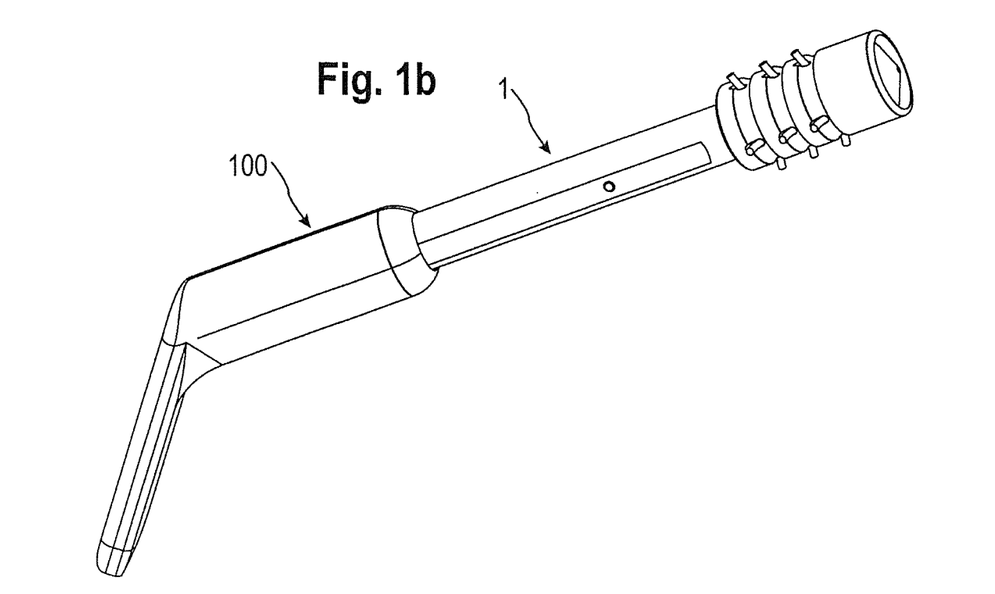
FIG. 1b shows a perspective view of the bone anchoring device in a second configuration according to the embodiment shown in FIG. 1a which is attached to the bone plate.

The bone anchoring device according to the invention and in particular the femur anchor can be used together with a bone plate as shown in FIGS. 1a and 1b, especially for use in osteoporotic bones. Also all further applications are conceivable in which the bone anchoring device can be used instead of conventional bone screws or instead of conventional pins used in a bone anchoring manner. It is also possible to provide rigid barb elements. In such a case the openings should be configured as long holes or recesses for guiding the barb elements.

Furthermore instead of the sleeve for supporting the screw together with the abutment portion other elements could be used which support the screw and allow the passing of the tool and the engagement with the engagement structure of the screw. For example, a snap ring could be. used.

What is claimed is:

1. A bone anchoring device for anchoring in a bone comprising:
   a hollow shaft having a proximal end, a distal end configured to be inserted into a bone before the proximal end and an outer surface comprising a first portion at the proximal end and a second portion at the distal end, the second portion having a larger outer diameter than the first portion; and
   a barb carrier comprising a shaft member, a head member, and at least two barb elements, wherein the barb carrier is configured to be secured inside the second portion with the head member forming an outside surface at the distal end of the hollow shaft, and each barb element is configured to project through the second portion;
   wherein the proximal end of the hollow shaft has an opening into the hollow shaft to receive a tool to move the barb carrier;
   wherein a length of the hollow shaft from the opening to the second portion is greater than a length of the second portion;
   wherein the hollow shaft and the barb carrier can be moved relative to each other in such a manner that in a first configuration the barb elements of the barb carrier project beyond an outer surface of the hollow shaft by a first distance;
   wherein the hollow shaft and the barb carrier can be moved relative to each other in such a manner that in a second configuration the barb elements of the barb carrier project beyond the outer surface of the hollow shaft by a greater amount than in the first configuration; and
   wherein the head member is configured to move in an axial direction of the hollow shaft when the barb carrier moves from the first configuration to the second configuration.

2. The bone anchoring device according to claim 1, wherein the bone anchoring device comprises a screw having a head, and the barb carrier comprises an inner thread, and wherein the movement from the first to the second configuration is achievable by rotating the screw.

3. The bone anchoring device according to claim 1, wherein the hollow shaft has a plurality of openings and wherein in the second configuration the barb elements are guided by the openings.

4. The bone anchoring device according to claim 3, wherein in the first configuration the barb elements are guided by the openings.

5. The bone anchoring device according to claim 1, wherein the head member includes a cone-shaped portion forming a tip of the bone anchoring device.

6. The bone anchoring device according to claim 1, wherein the barb carrier is a sleeve.

7. The bone anchoring device according to claim 1, wherein the barb elements are pins.

8. The bone anchoring device according to claim 1, wherein the barb elements and the barb carrier are integrally connected.

9. The bone anchoring device according to claim 1, wherein the barb elements are made of shape memory material.

10. The bone anchoring device according to claim 1, wherein the barb elements are arranged in a pinfeather- or arrow-like configuration, wherein free ends of the barb elements are directed toward the proximal end of the hollow shaft.

11. The bone anchoring device according to claim 2, wherein the screw is held axially fixed such as the screw only can perform a rotational movement.

12. The bone anchoring device according to claim 2, wherein the head of the screw is axially fixed between a first abutment and a second abutment.

13. The bone anchoring device according to claim 3, wherein the barb elements and the openings cooperate in such a manner, that the barb elements penetrate surrounding bone structure in the second configuration.

14. The bone anchoring device according to claim 2, wherein the head of the screw is axially fixed by at least one abutment.

15. The bone anchoring device according to claim 1, wherein a moving direction of the barb carrier from the first to the second configuration is against the insertion direction of the bone anchoring device.

16. The bone anchoring device according to claim 1, wherein the hollow shaft and the barb carrier can be moved relative to each other in such a manner that in a third configuration the barb elements of the barb carrier do not project beyond an outer surface of the hollow shaft.

17. A bone anchoring device for anchoring in a bone comprising:
   a hollow shaft having a proximal end, a distal end configured to be inserted into a bone before the proximal end and an outer surface comprising a threadless first portion;
   a barb carrier comprising a shaft member and a head member, wherein the head member has a larger outer diameter than the shaft member, and the head member is configured to be located at the distal end of the hollow shaft;
   at least two barb elements spaced apart along an axial direction, each barb element having a first end attached to the barb carrier and a second end opposite the first end;
   a screw configured to threadably engage with and move the barb carrier; and
   an abutment member configured to be inserted into the hollow shaft and fixed to the hollow shaft to maintain the abutment member at a fixed axial position within the hollow shaft, and to abut against the screw;
   wherein the hollow shaft and the barb carrier can be moved relative to each other in such a manner that in a first configuration the barb elements of the barb carrier project beyond an outer surface of the hollow shaft by a first distance; and wherein the hollow shaft and the barb carrier can be moved relative to each other in such a manner that in a second configuration the barb elements of the barb carrier project beyond the outer surface of the hollow shaft by a greater amount than in the first configuration.

18. The bone anchoring device according to claim 17, wherein the hollow shaft and the barb carrier can be moved relative to each other in such a manner that in a third configuration the barb elements of the barb carrier do not project beyond an outer surface of the hollow shaft.

19. A method of attaching a bone anchoring device to a bone or a vertebra, the bone anchoring device comprising a hollow shaft having a proximal end, a distal end configured to be inserted into a bone before the proximal end and an outer surface comprising a first portion at the proximal end and a threadless second portion at the distal end, the second portion having a larger outer diameter than the first portion; and
   a barb carrier comprising a shaft member, a head member, and at least two barb elements, wherein the barb carrier is configured to be secured inside the second portion with the head member forming an outside surface at the distal end of the hollow shaft, and each barb element configured to project through the second portion;
   wherein the proximal end of the hollow shaft has an opening into the hollow shaft to receive a tool to move the barb carrier;
   wherein a length of the hollow shaft from the opening to the second portion is greater than a length of the second portion;
   wherein the hollow shaft and the barb carrier can be moved relative to each other in such a manner that in a first configuration the barb elements of the barb carrier project beyond an outer surface of the hollow shaft by a first distance;
   wherein the hollow shaft and the barb carrier can be moved relative to each other in such a manner that in a second configuration the barb elements of the barb carrier project beyond the outer surface of the hollow shaft by a greater amount than in the first configuration; and
   wherein the head member is configured to move in an axial direction of the hollow shaft when the barb carrier moves from the first configuration to the second configuration, the method comprising:
   inserting the bone anchoring device into a bone, beginning with the distal end; and
   moving the barb carrier relative to the hollow shaft to move the barb carrier to the second configuration.

20. A bone anchoring device for anchoring in a bone comprising:
   a hollow shaft having a proximal end, a distal end configured to be inserted into a bone before the proximal end and an outer surface comprising a first portion at the proximal end and a second portion at the distal end, the second portion having a larger outer diameter than the first portion;
   a barb carrier comprising a shaft member and at least two barb elements, wherein the barb carrier is configured to be secured inside the second portion, a length of the shaft member is greater than a length of at least one of the barb elements, and each barb element is configured to project through the second portion; and
   a screw configured to threadably engage with and move the barb carrier;
   wherein the proximal end of the hollow shaft has an opening into the hollow shaft to receive a tool to move the barb carrier;
   wherein a length of the hollow shaft from the opening to the second portion is greater than a length of the second portion;
   wherein the hollow shaft and the barb carrier can be moved relative to each other in such a manner that in a first configuration the barb elements of the barb carrier project beyond an outer surface of the hollow shaft by a first distance; and
   wherein the hollow shaft and the barb carrier can be moved relative to each other in such a manner that in a second configuration the barb elements of the barb carrier project beyond the outer surface of the hollow shaft by a greater amount than in the first configuration.

21. A bone anchoring device for anchoring in a bone comprising:
   a hollow shaft having a proximal end, a distal end configured to be inserted into a bone before the proximal end and an outer surface comprising a first portion at the proximal end and a second portion at the distal end;
   a barb carrier;
   at least two barb elements spaced apart along an axial direction, each barb element having a first end attached to the barb carrier and a second end opposite the first end;
   a screw configured to threadably engage with and move the barb carrier; and
   an abutment member configured to be secured inside the first portion of the hollow shaft and fixed to the hollow shaft to maintain the abutment member at a fixed axial position within the hollow shaft, and to abut against the screw;
   wherein the hollow shaft and the barb carrier can be moved relative to each other in such a manner that in a first configuration the barb elements of the barb carrier project beyond an outer surface of the hollow shaft by a first distance; and
   wherein the hollow shaft and the barb carrier can be moved relative to each other in such a manner that in a second configuration the barb elements of the barb carrier project beyond the outer surface of the hollow shaft by a greater amount than in the first configuration.

* * * * *